(12) United States Patent
Yin et al.

(10) Patent No.: US 9,238,840 B2
(45) Date of Patent: Jan. 19, 2016

(54) METHOD FOR SINGLE CELL GENOME ANALYSIS AND KIT THEREFOR

(75) Inventors: Xuyang Yin, Guangdong (CN); Li Bao, Guangdong (CN); Xun Xu, Guangdong (CN); Hanjie Wu, Guangdong (CN); Xiaoyu Liu, Guangdong (CN); Xiuqing Zhang, Guangdong (CN); Huanming Yang, Guangdong (CN)

(73) Assignee: BGI-Shenzhen Co., Limited, Shenzhen (CN)

( * ) Notice: Subject to any disclaimer, the term of this patent is extended or adjusted under 35 U.S.C. 154(b) by 48 days.

(21) Appl. No.: 13/976,845

(22) PCT Filed: Dec. 29, 2011

(86) PCT No.: PCT/CN2011/084959
§ 371 (c)(1),
(2), (4) Date: Sep. 24, 2013

(87) PCT Pub. No.: WO2012/089148
PCT Pub. Date: Jul. 5, 2012

(65) Prior Publication Data
US 2014/0017683 A1    Jan. 16, 2014

(30) Foreign Application Priority Data
Dec. 31, 2010    (CN) .......................... 2010 1 0619689

(51) Int. Cl.
*C12Q 1/68*    (2006.01)

(52) U.S. Cl.
CPC ............ *C12Q 1/6888* (2013.01); *C12Q 1/6806* (2013.01); *C12Q 1/6851* (2013.01); *C12Q 1/6869* (2013.01); *C12Q 1/6876* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 6,673,541 B1 * | 1/2004 | Klein et al. ................. | 435/6.12 |
| 2003/0228613 A1 * | 12/2003 | Bornarth et al. ............. | 435/6 |
| 2004/0229233 A1 * | 11/2004 | Aburatani et al. ............ | 435/6 |
| 2006/0014167 A1 * | 1/2006 | Church et al. ............... | 435/6 |
| 2006/0172314 A1 * | 8/2006 | Song et al. ................ | 435/6 |
| 2007/0178457 A1 * | 8/2007 | Millar ..................... | 435/6 |
| 2009/0131275 A1 * | 5/2009 | Shimamoto et al. ........... | 506/17 |
| 2010/0267034 A1 | 10/2010 | Lo et al. | |
| 2011/0294167 A1 * | 12/2011 | McEwan et al. .............. | 435/91.2 |

FOREIGN PATENT DOCUMENTS

| | | |
|---|---|---|
| CN | 101137761 A | 3/2008 |
| CN | 101333561 A | 12/2008 |
| WO | WO-2009049889 A1 | 4/2009 |
| WO | WO-2010085498 A1 | 7/2010 |

OTHER PUBLICATIONS

Eisenberg et al. (Human housekeeping genes are compact, Trends Genet. Jul. 2003;19(7):362-5).*
Dheda et al. (Validation of housekeeping genes for normalizing RNA expression in real-time PCR, Biotechniques. Jul. 2004;37(1):112-4, 116, 118-9).*
Hosono et al. (Unbiased Whole-Genome Amplification Directly From Clinical Samples, Genome Res. May 2003;13(5):954-64. Epub Apr. 14, 2003).*
Wang et al. (DNA Degradation Test Predicts Success in Whole-Genome Amplification from Diverse Clinical Samples, J Mol Diagn. Sep. 2007;9(4):441-51. Epub Aug. 9, 2007).*
Fast DB ("Housekeeping Genes," attached, last updated Sep. 24, 2010, available at http://www.fast-db.com/fastdb2/frame.html, accessed Apr. 19, 2015).*
Nolan et al. (Quantification of mRNA using real-time RT-PCR, Nature Protocols, vol. 1, No. 3, Nov. 9, 2006).*
Rozen et al. (Primer3 on the WWW for General Users and for Biologist Programmers, in Methods in Molecular Biology, vol. 132: Bioinformatics Methods and Protocols, 2000).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
NCI Accession No. NM_004905.2 (Dec. 20, 2009 revision).*
Lubenow (The impact of whole genome amplification on forensic testing, Qiagen, Jun. 2006).*

(Continued)

*Primary Examiner* — Stephanie K Mummert
*Assistant Examiner* — Aaron Priest
(74) *Attorney, Agent, or Firm* — Drinker Biddle & Reath LLP (57) ABSTRACT

A method for analyzing a genome of a single cell is provided, and a kit is also provided. The method for analyzing the genome of the single cell may comprise separating and lysing the single cell to obtain a whole-genome DNA of the cell; subjecting the whole-genome DNA to a whole-genome amplification to obtain a whole-genome amplification product; performing a PCR amplification using the whole-genome amplification product as template and using housekeeping-gene-specific primers to detect the housekeeping gene of the whole-genome amplification product; and determining whether the whole genome amplification product meets a requirement for sequencing based on the detection result, wherein a uniform distribution of the amplification product in each chromosome is an indication of the amplification product meeting the requirement for sequencing.

6 Claims, 3 Drawing Sheets

(56) References Cited

OTHER PUBLICATIONS

Pan et al. (A procedure for highly specific, sensitive, and unbiased whole-genome amplification, Proc Natl Acad Sci U S A. Oct. 7, 2008;105(40):15499-504. Epub Oct. 1, 2008).*

Lasken et al. (Single-cell genomic sequencing using Multiple Displacement Amplification, Curr Opin Microbiol. Oct. 2007;10(5):510-6. Epub Oct. 17, 2007).*

Rodrigue et al. (Whole Genome Amplification and De novo Assembly of Single Bacterial Cells, PLoS One. Sep. 2, 2009;4(9):e6864).*

Pinard et al. (Assessment of whole genome amplification-induced bias through high-throughput, massively parallel whole genome sequencing, BMC Genomics. Aug. 23, 2006;7:216).*

Dean et al. (Comprehensive human genome amplification using multiple displacement amplification, Proc Natl Acad Sci U S A. Apr. 16, 2002;99(8):5261-6).*

Biology-Online Dictionary, definition of "housekeeping gene," attached, available at http://www.biology-online.org/dictionary/Housekeeping_genes, accessed Apr. 9, 2015.*

Marcy, Yann, et al., "Dissecting Biological "Dark Matter" with Single-Cell Genetic Analysis of Rare and Uncultivated TM7 Microbes from the Human Mouth", PNAS, vol. 104, No. 29, (2007), pp. 11889-11894.

Pinard, Robert, et al., "Assessment of Whole Genome Amplification-Induced Bias Through High-Throughput, Massively Parallel Whole Genome Sequencing", BMC Genomics, vol. 7, No. 216, (2006), 21 pages.

Marcy, Yann, et al., "Nanoliter Reactors Improve Multiple Displacement Amplification of Genomes from Single Cells", PLoS Genetics, vol. 3, Issue 9, (2007), pp. 1702-1708.

Dean, Frank B., et al., "Comprehensive Human Genome Amplification Using Multiple Displacement Amplification", PNAS, vol. 99, No. 8, (2002), pp. 5261-5266.

Eisenberg, Eli, et al., "Human Housekeeping Genes are Compact", Trends in Genetics, vol. 19, No. 7, (2003), pp. 362-365.

Paired-End Sequencing Sample Preparation Guide, Illumina Proprietary, Catalog #PE-930-1001, Part # 1005063 REv. B, (2009), 34 pages.

Zhang, Lin, et al., "Whole Genome Amplification from a Single Cell: Implications for Genetic Analysis", Proc. Natl. Acad. Sci. USA, vol. 89, (1992), pp. 5847-5851.

* cited by examiner

Relationship between Chr1 sequencing depth
and GC content in human single depth

METHOD FOR SINGLE CELL GENOME ANALYSIS AND KIT THEREFOR

CROSS-REFERENCE TO RELATED APPLICATIONS

This application is a national stage application (under 35 U.S.C. §371) of PCT/CN2011/084959, filed Jun. 29, 2011, which claims priority to and benefit of Chinese Patent Application Serial No. 201010619689.8, filed with the State Intellectual Performance Office (SIPO) of P. R. China on Dec. 31, 2010, in which the entire contents of both are incorporated herein by reference.

FIELD

The present disclosure relates to the field of molecular cell biology, more particularly to the field of single cell genome of higher organisms. Specifically, the present disclosure relates to a method for analyzing single cell genome and a kit thereof.

BACKGROUND

There exists heterogeneity between different parts of the same tissue and individuals of different tissues. Likewise, there exists heterogeneity between different cells, even the cell population with exactly same genetic background cultured in vitro. Therefore, developing a technique method applying to single cell study to reveal a regular pattern of cell heterogeneity is important for better cell biology research. Thus, some researchers have proposed a concept of "single cell analysis". While in the single cell analysis, the study on a single cell genome is the current focus of research.

At present, study of micro-DNA and single cell genome has been widely used in archeology, microbial ecology, medical testing, forensic testing, clinical diagnosis and various scientific researches (refers to Zhang L., Cui X., Schmitt K., Hubert R., Navidi W., Arnheim N. (1992) Whole genome amplification from a single cell: Implication for genetic analysis, Proc Natl Acad Sci USA: 5847-5851, which is incorporated herein by reference). Analysis and study of the single cell genome of higher plants and animals may be efficiently and conveniently used in clinical diagnosis and treatment (for example, prenatal diagnosis, pre-implantation genetic diagnosis, multi-point mapping, typing for sperm and eggs, diagnosis of genetic disease, etc.), medical research (for example, research of autism, neurological diseases and autoimmune diseases, research of genome variation, and stem cell research, etc.), archaeological research and forensic detection. However, studies and reports about the single cell genome of higher organisms such as mammals are rare.

Therefore, currently the method for analyzing the single cell genome still needs to be improved.

SUMMARY

The present disclosure has been accomplished based on the following findings of inventor:

Currently, single cell genome analysis is performed mainly by sequencing a single cell genome. Since, commonly-used DNA analysis method such as comparative genomic hybridization (Comparative Genomic Hybridization, CGH), polymerase chain reaction (Polymerase Chain Reaction, PCR), gene chip (DNA Microarray), restricted fragment length polymorphisms analysis (Restricted Fragment Length Polymorphisms, RFLP) and single strand conformation polymorphism (SSCP), fingerprint technology and fluorescence in situ hybridization (Fluorescence in Situ Hybridization, FISH), etc., can only be used in study of part of the single cell genome or known sites, and it is a lack of effective strategy for a genome study of a new species. While sequencing the single genome may effectively avoid these deficiencies.

But, the amount of single-cell-genome DNA is at picogram level, while currently a starting amount required for DNA sequencing technology is at microgram level, thus the single cell genome needs to be subjected to a whole-genome-amplification (WGA) to achieve a sufficient amount.

However, known whole-genome-amplification method which comprises PCR-based methods (such as PEP-PCR and DOP-PCR) and multiple displacement amplification (MDA, Multiple Displacement Amplification) is susceptible to many interfering factors which cannot guarantee 100% successful rate of amplification.

The present disclosure is directed to solve at least one of the problems existing in the art. Accordingly, the present disclosure provides a method for analyzing a genome of a single cell and a kit thereof, so as to make a whole-genome-amplification product of the single cell genome be detected and screened before subjecting to sequencing. Thereby an unsuccessfully amplified sample is removed which guarantee a pass rate of follow-up single cell genome sequencing.

According to one aspect of the present disclosure, the present disclosure provides the method for analyzing the genome of the single cell. According to embodiments of the present disclosure, the method comprises the steps of: separating and lysing the single cell to obtain a whole-genome DNA of the cell; subjecting the whole-genome DNA to a whole-genome amplification to obtain a whole-genome amplification product; performing a PCR amplification using the whole-genome amplification product as template and using housekeeping-gene-specific primers to detect the housekeeping gene of the whole-genome amplification product; and determining whether the whole genome amplification product meets a requirement for sequencing based on the detection result, wherein a uniform distribution of the amplification product in each chromosome is an indication of the amplification product meeting the requirement for sequencing.

The inventor has surprisingly found out that using the method for analyzing the genome of the single cell according to embodiments of the present disclosure to analyze the single cell of the higher organisms, may effectively obtain the whole-genome amplification product of the single cell to be test, which is in accordance with the indication of the requirement for sequencing. Further, the amplification product may be effectively used in constructing a genome sequence library of the single cell to be test, and the obtained sequence library may be effectively used in high-throughput sequencing platforms such as a SOLEXA® sequencing platform. Thereby base on sequencing results, a genome DNA sequence information of the single cell to be test may be effectively obtained. And then based on these information, it may be effectively used in follow-up analysis and study of the single cell genome deeper.

According to another aspect of the present disclosure, the present disclosure provides a kit. According to embodiments of the present disclosure, the kit may comprise housekeeping-gene specific primers. The inventor has found out that using the kit according to embodiments of the present disclosure may effectively obtain the whole-genome amplification product of the single cell of higher organisms, which is in accordance with the indication of the requirement for sequencing. And then a sequence library is constructed by using the amplification product, and the obtained library is subjected to high-throughput sequencing. Thereby base on sequencing results, a genome DNA sequence information of the single cell to be test may be effectively obtained. And then based on these information, it may be achieve the genome analysis of the single cell to be test.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

It should be noted that, in the description of the present disclosure, unless otherwise noted, "plurality" means two or two more.

Method for Analyzing Single Cell Genome

According to one aspect of the present disclosure, the present disclosure provides a method for analyzing a genome of a single cell. According to embodiments of the present disclosure, the method may comprise steps of:

Firstly, the single cell is separated and lysed to obtain a whole-genome DNA of the cell.

Secondly, the whole-genome DNA is subjected to a whole-genome amplification to obtain a whole-genome amplification product. According to embodiments of the present disclosure, the method of subjecting the whole-genome DNA to whole-genome amplification to obtain a whole-genome amplification product is not specially restricted. According to one specific example of the present disclosure, the whole-genome amplification may involve multi-displacement amplification MDA or DOP-PCR whole-genome amplification to perform the single cell whole-genome amplification.

Thirdly, a PCR amplification using the whole-genome amplification product as template and using housekeeping-gene-specific primers is performed to detect the housekeeping gene of the whole-genome amplification product. According to embodiments of the present disclosure, a source of the single cell is not specially restricted. According to one specific example of the present disclosure, the single cell is a human single cell, the housekeeping gene is at least one selected from a group consisting of PRDX6, RPL37a, ADD1, HLA-A, RAD9A, ARHGEF7, EIF2B2, PSMD7, BCAT2 and ATP5O. According to some specific examples of the present disclosure, for PRDX6, the housekeeping-gene-specific primers have nucleotide sequences shown as SEQ ID NO:1 and SEQ ID NO:2, respectively; for RPL37a, the housekeeping-gene-specific primers have nucleotide sequences shown as SEQ ID NO:3 and SEQ ID NO:4, respectively; for ADD1, the housekeeping-gene-specific primers have nucleotide sequences shown as SEQ ID NO:5 and SEQ ID NO:6, respectively; for HLA-A, the housekeeping-gene-specific primers have nucleotide sequences shown as SEQ ID NO:7 and SEQ ID NO:8, respectively; for RAD9A, the housekeeping-gene-specific primers have nucleotide sequences shown as SEQ ID NO:9 and SEQ ID NO:10, respectively; for ARHGEF7, the housekeeping-gene-specific primers have nucleotide sequences shown as SEQ ID NO:11 and SEQ ID NO:12, respectively; for EIF2B2, the housekeeping-gene-specific primers have nucleotide sequences shown as SEQ ID NO:13 and SEQ ID NO:14, respectively; for PSMD7, the housekeeping-gene-specific primers have nucleotide sequences shown as SEQ ID NO:15 and SEQ ID NO:16, respectively; for BCAT2, the housekeeping-gene-specific primers have nucleotide sequences shown as SEQ ID NO:17 and SEQ ID NO:18, respectively; for ATP5O, the housekeeping-gene-specific primers have nucleotide sequences shown as SEQ ID NO:19 and SEQ ID NO:20, respectively.

Fourthly, whether the whole-genome amplification product meets the requirement for sequencing is determined based on the detection result, in which a uniform distribution of the amplification product in each chromosome is an indication of the amplification product meeting the requirement for sequencing. The expression used herein "a uniform distribution of the amplification product in each chromosome is an indication of the amplification product meeting the requirement for sequencing" refers to that when using housekeeping-gene-specific primer and using the whole-genome amplification product as temple to perform PCR amplification, if all housekeeping genes which are corresponding with the housekeeping-gene-specific primers and distributed in different chromosomes has been amplified effectively, it indicates that the whole-amplification product obtained from the above single cell is uniformly distributed in each chromosome, thereby it demonstrates that the effect of the whole genome amplification is good and the amplification product may meet the follow-up sequencing requirement, as a result it can be say that a uniform distribution of the amplification product in each chromosome is an indication of the amplification product meeting the requirement for sequencing. According to specific examples of the present disclosure, the method for analyzing the genome of the single cell of the present disclosure may further comprise constructing a DNA sequence library of the amplification product. According to some embodiments of the present disclosure, the method may also further comprise sequencing the DNA sequence library. In addition, according to some embodiment of the present disclosure, the method may subject the whole-genome amplification product to housekeeping gene quantitative detection.

The inventor has surprisingly found out that using the method for analyzing the genome of the single cell according to embodiments of the present disclosure to analyze the single cell of the higher organisms, may effectively obtain the whole-genome amplification product of the single cell to be test, which is in accordance with the indication of the requirement for sequencing. Further, the amplification product may be effectively used in constructing a genome sequence library of the single cell to be test, and the obtained sequence library may be effectively used in high-throughput sequencing platforms such as Solexa sequencing platform. Thereby base on sequencing results, a genome DNA sequence information of the single cell to be test may be effectively obtained. And then based on these information, it may be effectively used in follow-up analysis and study of the single cell genome deeper.

Specifically, according to some embodiments of the present disclosure, the method for analyzing the genome of the single cell of the present disclosure may comprise the steps of:
- a. separating and lysing the single cell to obtain an entire genome DNA of the cell;
- b. subjecting the entire genome DNA of the cell to a whole-genome amplification to obtain a whole-genome amplification product;
- c. subjecting the whole-genome amplification product to the quantitative detection and a qualitative detection, the qualitative detection refers to using housekeeping-gene (Housekeeping Gene) detection method to detect the whole-genome amplification product, in which, a uniform distribution of the amplification product in each chromosome is an indication of the amplification product meeting the requirement for sequencing.

According to embodiments of the present disclosure, the method may also comprise step d: constructing a DNA sequencing library of the qualified amplification product and sequencing.

According to some embodiments of the present disclosure, preferably, the whole-genome amplification of the single cell in step b may involve multi-displacement amplification MDA or DOP-PCR whole-genome amplification.

According to embodiments of the present disclosure, in step c, the used housekeeping-gene detection refers to that using the housekeeping-gene-specific primer and using the whole-genome amplification product as template to perform PCR amplification.

According to some specific examples of the present disclosure, preferably, the single cell is the human single cell, the housekeeping gene is at least one selected from a group consisting of PRDX6 located at 1# chromosome, RPL37a located at 2# chromosome, ADD1 located at 4# chromosome, HLA-A located at 6# chromosome, RAD9A located at 11# chromosome, ARHGEF7 located at 13# chromosome, EIF2B2 located at 14# chromosome, PSMD7 located at 16# chromosome, BCAT2 located at 19# chromosome, and ATP5O located at 21# chromosome.

According to some embodiment of the present disclosure, preferably, for PRDX6, the housekeeping-gene-specific primers have nucleotide sequences shown as SEQ ID NO: 1 and SEQ ID NO:2, respectively; for RPL37a, the housekeeping-gene-specific primers have nucleotide sequences shown as SEQ ID NO:3 and SEQ ID NO:4, respectively; for ADD1, the housekeeping-gene-specific primers have nucleotide sequences shown as SEQ ID NO:5 and SEQ ID NO:6, respectively; for HLA-A, the housekeeping-gene-specific primers have nucleotide sequences shown as SEQ ID NO:7 and SEQ ID NO:8, respectively; for RAD9A, the housekeeping-gene-specific primers have nucleotide sequences shown as SEQ ID NO:9 and SEQ ID NO:10, respectively; for ARHGEF7, the housekeeping-gene-specific primers have nucleotide sequences shown as SEQ ID NO:11 and SEQ ID NO:12, respectively; for EIF2B2, the housekeeping-gene-specific primers have nucleotide sequences shown as SEQ ID NO:13 and SEQ ID NO:14, respectively; for PSMD7, the housekeeping-gene-specific primers have nucleotide sequences shown as SEQ ID NO:15 and SEQ ID NO:16, respectively; for BCAT2, the housekeeping-gene-specific primers have nucleotide sequences shown as SEQ ID NO:17 and SEQ ID NO:18, respectively; for ATP5O, the housekeeping-gene-specific primers have nucleotide sequences shown as SEQ ID NO:19 and SEQ ID NO:20, respectively.

More specifically, according to some embodiments of the present disclosure, the method for analyzing the genome of the single cell of the present disclosure may also comprise steps of:

(1) Separation of the Single Cell:

It may involve physical-mechanical method, chemical method, or biological method, for example methods of microfluidic flow cytometry, mouth-controlled pipette separation, gradient dilution or low melting point agarose fixing, etc., a single cell containing an entire genome is obtained after separation.

(2) Lysing the Cell:

It may involve methods of detergent, boiling, alkaline denaturation, lysozyme or organic solvents, etc. to lyse cell nuclei of the obtained single cell by separation, so as to obtain the entire genome DNA of the cell.

Figure 6:
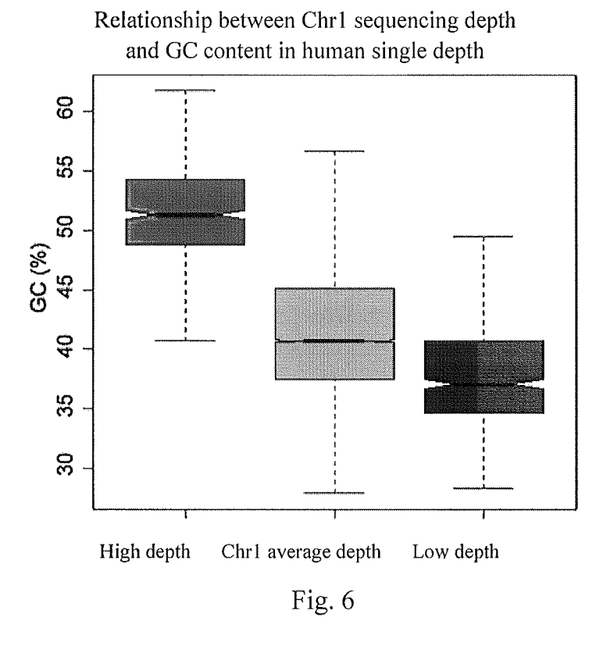
FIG. 6 is relationship chat between sequencing depth 1# chromosome and GC content in human single cell according to one embodiment of the present disclosure.

(3) Whole-Genome Amplification (WGA) of the Single Cell:

The obtained genome DNA of the cell is subjected to the whole-genome amplification of the single cell to obtain a whole-genome amplification product, so as to achieve a DNA starting amount required for new generation sequencing technique. Recently, there are two strategies of the whole-genome amplification, eg. PCR-based amplification and linear DNA amplification, the former mainly comprises DOP-PCR, PEP-PCR, T-PCR; the latter mainly comprises OmniPlex WGA, multiple displacement amplification (MDA). According to embodiments of the present disclosure, the multiple displacement amplification (MDA) or DOP-PCR are preferably involved in the whole-genome amplification of the single cell. When involving the multiple displacement amplification (MDA) to perform the whole-genome amplification of the simple cell, MDA may involve a primer completely composed of a random nucleotide; the primer may have a length of about 5-20 nucleotide; a GC content of the primer may be selected in accordance with the template property. The property of the template is mainly restricted to the GC content of the DNA template, so it is appropriate to choose the GC content of the primer which is close to or same to the template, for example when using the human genome DNA as template to perform MDA, it may choose the random primer having a GC content of about 40%-42%. While a bias of the whole genome amplification is affected by the GC content, for example, as shown in FIG. 6, using human genome DNA as the template, when involving the random primer with 50% GC content to perform MDA amplification, the region with more amplification-copy-number are the region with high GC content.

(4) Quantification of the Whole-Genome Amplification Product:

It may involve methods of gel electrophoresis detection, Agilent 2100 Bioanalyzer detection, QUANT-iT™ dsDNA BR detection kit to quantify the obtained whole-genome amplification product; the results show that only the whole-genome amplification product without degradation and meeting the DNA starting amount required for new generation sequencing technique may proceed to construct a DNA library and be sequencing on a machine. While the strategy of constructing the library may be different due to the different DNA starting amount required for the new generation sequencing technique, generally the DNA starting amount required for constructing a library of DNA small fragment is more than 1 µg.

(5) Detection of Whole-Genome Amplification Product:

It may involve a housekeeping-gene detection method to detect the obtained whole-genome amplification product; the results show that only the amplification product which is evenly distributed in chromosome of corresponding species may proceed to construct a DNA library and be sequencing on a machine. The step is a screening step for the whole-genome amplification product of the single cell to remove a large of unqualified amplification products, so as to control the quality of downstream sequencing-library on a machine, thus it may avoid unnecessary waste to a great extent.

(6) DNA Library Construction and Sequencing on Instrument Platform:

It may involve conventional technique of whole-genome DNA library construction or exon sequence capture to construct the DNA library with the whole-genome amplification product which is detected to be qualified. According to embodiments of the present disclosure, it may involve method known to those skilled in the mi, for example, using an ILLUMINA® library construction method to construct the DNA library. And then, the obtained library is subjected to quality detection which comprises QPCR detection and AGILENT 2100 BIOANALYZER® detection. For AGILENT 2100 BIOANALYZER® detection, it is required that the difference between library fragment size and expected size is less than ±10 bp without entrainment; QPCR detection for the concentration of the library, it is required that the total amount calculated in accordance with the library concentration achieves the requirement of sequencing. The qualified library by detection is subjected to genome sequencing of the single cell using the new generation sequencing technique. According to embodiments of the present disclosure, it may involve at least one sequencing system selected from a group of ILLUMINA HISEQ 2000® sequencing system, ILLUMINA GENOME ANALYZER II® sequencing system, AB SOLiD™ 4.0® sequencing system and ROCHE GS FLX TITANIUM® sequencing system to obtain the sequencing results.

(7) Bioinformatics Analysis

Based on the bioinformatics analysis of the sequencing result, the genome of the single cell is subjected to sequencing information analysis and study to obtain a genetic variation information of the single cell genome, such as a single nucleotide polymorphisms (SNP) of a related gene, an insertion and deletion (InDel) of a minority base, copy number variation (CNV) of the DNA and structural variation (SV), etc.

According to embodiments of the present disclosure, the method for analysing the single cell genome of the present disclosure, by subjecting the genomic DNA of the single cells of higher organisms to the whole-genome amplification, and introducing the steps of quantitative and qualitative detection after amplification, it may make the sample tested to be qualified to proceed next steps of the library construction and the sequencing by the new generation sequencing technique (NGS), so as to achieve accurate and efficient analysis of the single cell genome. The inventor has surprisingly found out that the method for analysing the single cell genome of the present disclosure is simple, efficient and time-saving. Using the method may effiently analyze and study the single cell genome of the higher plants and animals, and may completely analyze the genetic variation information of the single cell genome, which may effectively avoid the lack of conventional DNA analysis method that can only study a partial region of the single cell genome. And the introduced screening steps of quantitative and qualitative detection may remove a large of unqualified amplification products to control the quality of downstream sequencing-library on sequencer, thus it may avoid unnecessary waste to a great extent. In addition, the method for analysing the single cell genome of the present disclosure also has provided effective research strategy for study on single cell genome of new species.

Kit

According to another aspect of the present disclosure, the present disclosure has provided a kit. According to embodiments of the present disclosure, the kit comprises housekeeping-gene-specific primers. According to one specific example of the present disclosure, the housekeeping gene is at least one selected from a group consisting of PRDX6, RPL37a, ADD1, HLA-A, RAD9A, ARHGEF7, EIF2B2, PSMD7, BCAT2 and ATP5O. According to some embodiments of the present disclosure, the housekeeping-gene-specific primers comprised in the kit of the present disclosure may be: for PRDX6, the housekeeping-gene-specific primers have nucleotide sequences shown as SEQ ID NO:1 and SEQ ID NO:2, respectively; for RPL37a, the housekeeping-gene-specific primers have nucleotide sequences shown as SEQ ID NO:3 and SEQ ID NO:4, respectively; for ADD1, the housekeeping-gene-specific primers have nucleotide sequences shown as SEQ ID NO:5 and SEQ ID NO:6, respectively; for HLA-A, the housekeeping-gene-specific primers have nucleotide sequences shown as SEQ ID NO:7 and SEQ ID NO:8, respectively; for RAD9A, the housekeeping-gene-specific primers have nucleotide sequences shown as SEQ ID NO:9 and SEQ ID NO:10, respectively; for ARHGEF7, the housekeeping-gene-specific primers have nucleotide sequences shown as SEQ ID NO: 11 and SEQ ID NO:12, respectively; for EIF2B2, the housekeeping-gene-specific primers have nucleotide sequences shown as SEQ ID NO:13 and SEQ ID NO:14, respectively; for PSMD7, the housekeeping-gene-specific primers have nucleotide sequences shown as SEQ ID NO:15 and SEQ ID NO:16, respectively; for BCAT2, the housekeeping-gene-specific primers have nucleotide sequences shown as SEQ ID NO:17 and SEQ ID NO:18, respectively; for ATP5O, the housekeeping-gene-specific primers have nucleotide sequences shown as SEQ ID NO:19 and SEQ ID NO:20, respectively. According to specific examples of the present disclosure, the kit of the present disclosure may further comprise a reagent adapted for the whole amplifying a single cell by multiple displacement amplification MDA or DOP-PCR.

The inventor has found out that using the kit according to the embodiments of the present disclosure may effectively obtain the whole genome amplification product meeting the requirement for sequencing indicator of the single cell of higher organisms. And then by using the amplification product to construct DNA sequencing library and subjecting the obtained DNA sequencing library to a high-throughput sequencing, based on the sequencing results, it may accurately and effectively obtain a genomic DNA sequencing information of the single cell to be detected, and a genetic variation information of the single cell genome, such as a single nucleotide polymorphisms (SNP) of a related gene, an insertion and deletion (InDel) of a minority base, copy number variation (CNV) of the DNA and structural variation (SV), etc. Thereby based on these information, it may effectively achieve a deeper analysis of the single cell genome to be detected.

The inventor has found out that, using the method for analyzing the genome of the single cell and the kit of the present disclosure, it may efficiently analyze and study the single genome of higher plants and animals; and it may efficiently and conveniently applied to clinic diagnosis and treatment (for example, prenatal diagnosis, pre-implantation genetic diagnosis, multi-point mapping, typing for sperm and eggs, diagnosis of genetic disease, etc.), medical research (for example, research of autism, neurological diseases and autoimmune diseases, research of genome variation rate, and stem cell research, etc.), archaeological research and forensic detection.

It should be noted that the method for analyzing the genome of the single cell and the kit according to the embodiments of the present disclosure are completed through hard creative labor and optimization work by the inventor of the present application.

Reference will be made in detail to embodiments of the present disclosure. It would be appreciated by those skilled in the art that the following embodiments are explanatory, and cannot be construed to limit the scope of the present disclosure. Embodiments do not indicate the specific technology or conditions, will be performed in accordance with the techniques or conditions described the literature in the art (for example, referring to J. Sambrook, et al, <Molecular Cloning Laboratory Manual> translated by Huang PT, third version, science Press) or in accordance with the product instructions. Reagents or instruments do not label manufacturer, are both common products can be purchased commercially, such as purchased from ILLUMINA® company.

Example 1

Study on Human Single Cell Genome separating and lysing the single cell: the single cell of immortalized human lymphocyte was added to PBS droplets on a plate, and was diluted properly (eg. being diluted according to the concentration of the cell line until the cell number observed within the view of the microscope 200× was between 10 to 20), then was separated to single cell by aspiration under the microscope. The obtained single cell was put into a PCR tube containing 1.5-2 μL ALB (Alkaline Lysis Buffer, a specific formulation is: 50 mM DTT, 200 mM KOH). And the PCR tube containing the single cell and the ALB was place at −20° C. to −80° C. for 30 minutes The PCR tube containing the single cell was heated up to about 62-68° C., preferably the single cell was heated up to 65° C. for about 8-12 minutes to lyse the cell and release the whole-genome DNA of the cell.

(2) Whole Genome Amplification (WGA)

It may involve at least one means selected from the groups of multiple displacement amplification MDA and DOP-PCR whole-genome amplification to amplify the whole genome of the cell.

(1) Multiple Displacement Amplification (MDA)

The following reagents were prepared according to the production manual:

Buffer D1 (Qiagen REP LI-g Mini Kit):

| Reconstructed buffer DLB | 9 μL |
| Nuclease-free water (Nuclease-free water) | 32 μL |

500 μL nuclease-free water was added to DLB buffer. They were mixed evenly be shakings, then with a brief centrifuge to avoid unevenly mixture due to droplet being attached on tube wall. Then a reconstructed buffer DLB was obtained. The DLB buffer was sensitive to pH value, so it should be avoided with $CO_2$ in air to neutralize. The reconstructed buffer DLB could be stored at −20° C. for 6 months.

Buffer N1 (Qiagen REP LI-g Mini Kit):

| Stop solution (Stop solution) | 12 μL |
| Nuclease-free water | 68 μL |

2.5 μl buffer D1 was added to the whole-genome DNA of the cell obtained in the above step (1). They were place at room temperature for about 3-5 minutes to denature DNA. Then 5 μL, buffer N1 was added to neutralize the above buffer and stop the denaturing reaction, so as to obtain a DNA template of the single cell. The obtained buffer was place at room temperature for later usage.

The MDA reaction may involve at least one selected from the following two products:

NEB Company phi29 DNA polymerase products:

| Reagent | |
| --- | --- |
| N6 primer | 2.5 μL |
| 10X Phi29 DNA polymerase buffer | 2 μL |
| dNTP mixture | 2 μL |
| Phi 29 polymerase | 1 μL |
| 100X BSA | 0.4 μL |
| ddH$_2$O | up to 10 μl |

The above system may be according to the needs of the total volume size to increase or decrease each component in accordance with the same proportion.

QIAGEN REPLI-g® Mini Kit:

| ddH$_2$O | 10 μL |
| Reaction buffer | 29 μL |
| REPLI-g DNA polymerase | 1 μL |

The above system may be according to the needs of the total volume size to increase or decrease each component in accordance with the same proportion.

At least one selected from the above two reaction systems was added to the PCR tube containing the single cell DNA template (the product by adding the buffer D1 to denaturation and adding the buffer N1 to stop the denaturing reaction). They were mixed evenly, then with a brief centrifuge to avoid unevenly mixture due to droplet being attached on tube wall. Then the PCR tube was placed onto a PCR instrument to incubate at a constant temperature of 30° C. for about 10 to 16 hours, and then the Phi29 ploymerase was inactivated at 65° C.

(2) DOP-PCR Whole-Genome Amplification:

The whole-genome DNA obtained in the above step (1) was subjected to DOP-PCR whole-genome amplification by using GENOMEPLEX® Single Cell Whole Genome Amplification (WGA) Kit from Sigma Company. Firstly, the PCR tube containing the single cell DNA was added with ddH$_2$O up to 94, then 1 µL 10× single cell lysis buffer and fragmentation buffer (10× Single Cell Lysis & Fragmentation Buffer) was added to the above PCR tube. Then the PCR tube was placed at 99° C. for 4 minutes to break genome DNA of the cell. Then a QmniPlex library was constructed according to the specification, and a linear-isothermal starting amplification and PCR amplification were performed.

Another option, the whole-genome DNA of the cell obtained in the above step (1) was subjected to the DOP-PCR whole-genome amplification according to the manual of PicoPlex WGA Kit from Rubicon Genomics Company.

(3) Concentration Detection of the Whole-Genome Amplification Product

The concentration of the whole-genome amplification product was detected according to the kit specification by using a Quant-iT™ dsDNA BR detection Kit. When the content of the amplification product was more than 2 µg, the amplification product may proceed to DNA library construction and sequencing on sequencer.

(4) DNA Library Construction and Sequencing on Machine:

It may involve conventional technique of whole-genome DNA library construction or exon sequence capture (Exon Capture) to construct the DNA library. And then the qualified library after detection was subjected to single cell genomic sequencing on ILLUMINA HISEQ 2000® sequencing system.

(5) Bioinformatics Analysis

Figure 1:
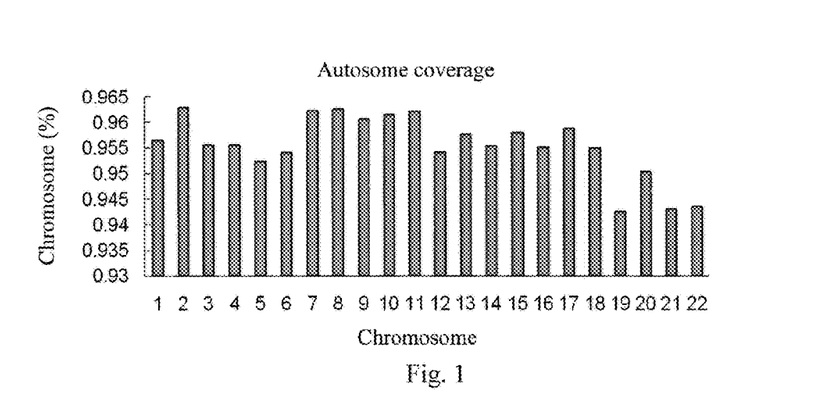
FIG. 1 is a coverage situation in each autosome of human single cell genome sequencing data according to one embodiment of the present disclosure.
Figure 2:
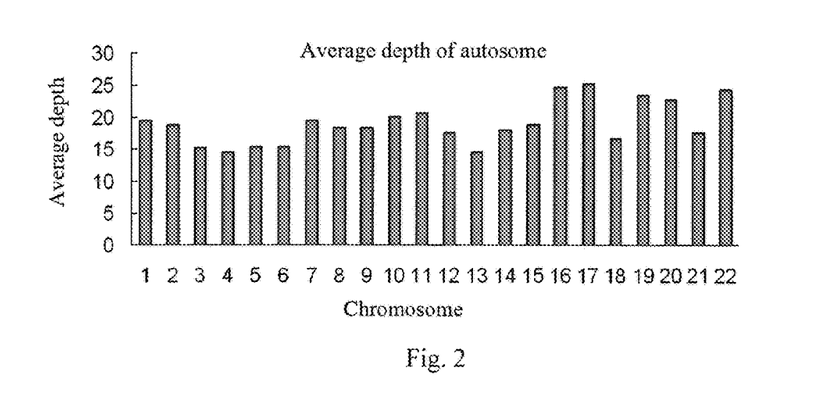
FIG. 2 is an average sequencing depth in each autosome of human single cell genome sequencing data according to one embodiment of the present disclosure.
Figure 3:
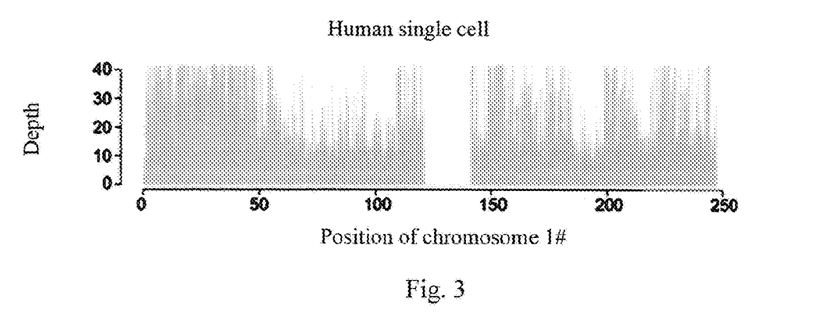
FIG. 3 is a distribution of human single cell genome sequence depth taken the 1# chromosome as an example according to one embodiment of the present disclosure.
Figure 4:
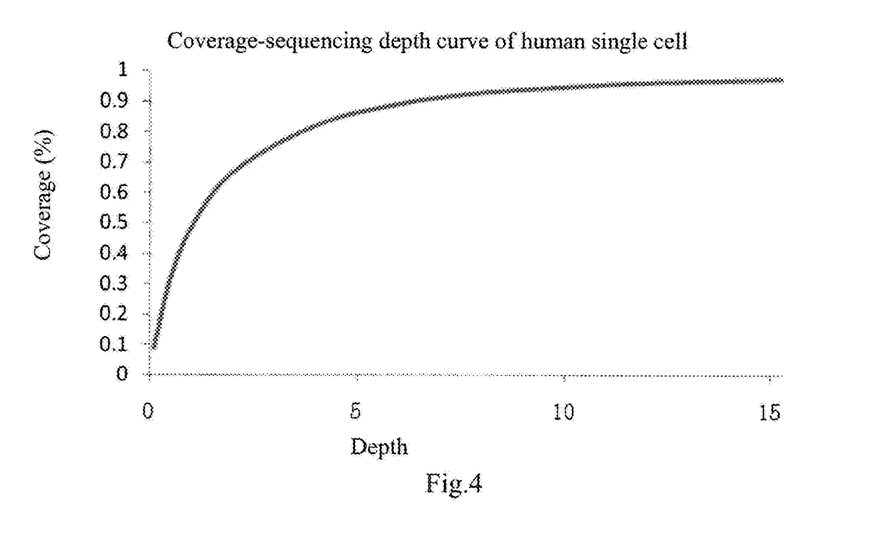
FIG. 4 is a relationship chat between the coverage and the sequencing depth in human single cell genome sequencing data according to one embodiment of the present disclosure.

After the above whole-genome deep sequencing of human single cell library by HISEQ 2000® system, the sequencing result was obtained, in which 35 Gb data could be match to the reference sequence in NCBI. The average sequencing depth was 13.3× ("sequencing depth" refers to the sequencing number of each nucleotide in the genome). The coverage rate of the genome sequencing data in each autosome of the human single cell and the average depth were shown in FIG. 1 and FIG. 2. The depth distribution in 1# autosome was shown in FIG. 3. The relationship between the coverage and the sequencing depth in human genome was shown in FIG. 4. FIG. 3 was a statistic of sequencing average depth in term of 10 k length of the chromosome and performed charting. As can be seen from the FIG. 3, there were significant difference between the sequencing depths of human single cell genomic sequencing data in different regions of the chromosome. As can be seen from the FIG. 4, as the sequencing depth increased, the coverage rate also increased, but with a smaller slope and gradually achieve a platform. When the sequencing depth was 7×, the coverage rate could achieve to 90%; and when the sequencing depth was 10×, the coverage rate could achieve to 95%.

Figure 5:
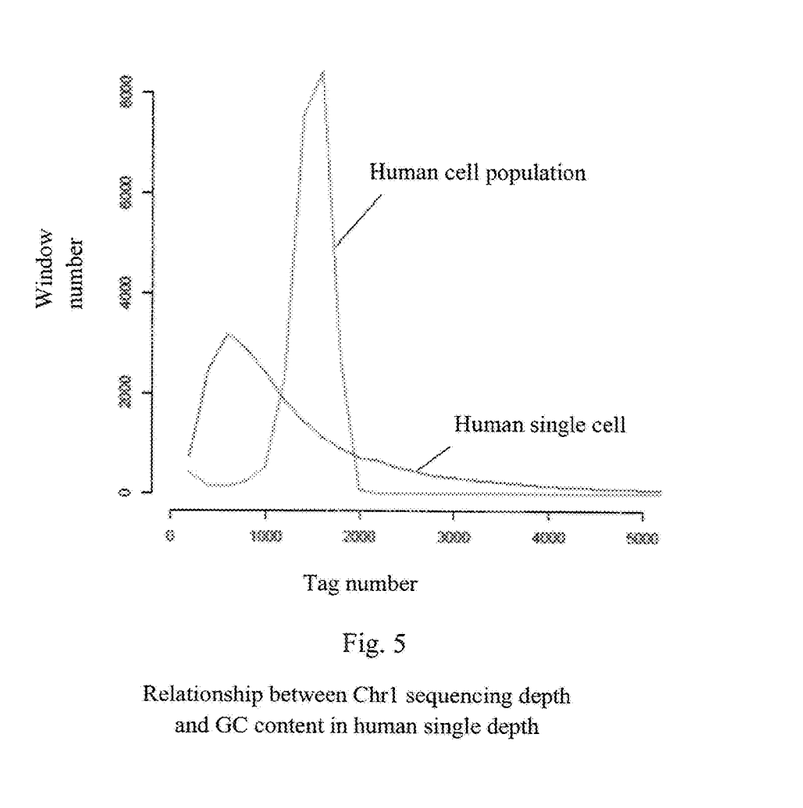
FIG. 5 is a bias analysis chart between human single cell genome sequencing data and human cell population data obtained according to one embodiment of the present disclosure.

In addition, the obtained human single cell genomic sequencing data was analyzed and plotted with a human cell population. The specific method was: taken the 1# chromosome as an example, taken the 20 kb as a window, a Tag number of each window (Tag number) was calculated, and then the window number was plotted with corresponding Tag number, the results was shown in FIG. 5. Generally in a certain range of the Tag number the window number was the most, thus it would form a peak. It can be seen from the FIG. 5, the Tag number peak position of all human single genomic sequencing data was obvious deviated from the cell population data, which indicated that the genome of the single cell existed bias after amplification.

Then, based on the obtained human single cell genomic sequencing data, taken the 1# chromosome as an example, the average depth was calculated by taken the 10 k as a window. Then the windows having 2.5% highest depth or 2.5% lowest depth respectively were selected to calculate GC % distribution of the above two. And it was plotted compared with GC % of the whole chromosome, the result was shown in FIG. 6. As shown in FIG. 6, GC % of high-depth region was significantly higher than the entire level; GC % of low-depth region was significantly lower than the entire level, which indicated that the sequencing depth of the single cell genome was affected by GC content.

In addition, by analyzing the sequencing data of human single genome, the genetic variation information of the single cell genome was also obtained, for example, the single nucleotide polymorphisms (SNP) of the related gene, the insertion and deletion (InDel) of the minority base, copy number variation (CNV) of the DNA and structural variation (SV), etc.

Example 2

Subjecting a Single Cell WGA Product to Housekeeping Detection by Using Human Housekeeping Gene Primer Referred to the method in EXAMPLE 1, a single cell was separated from human tissue or blood, and was subjected to lysis and WGA treatment to obtain a single cell WGA product. Then, using a housekeeping-gene-specific primer, the obtained single WGA product was subjected to PCR amplification, so as to achieve the housekeeping gene detection. The PCR amplification system contained: heat-resisting DNA polymerase with 3' exo-nuclease activity; single cell WGA product (template DNA); dNTP mixture, Mg$^{2+}$; monovalent cation; housekeeping-gene-specific primer. Specifically, the PCR amplification reaction system was as following:

| | |
|---|---|
| Taq DNA polymerage | 0.1 U/µL; |
| Tempelate DNA | 15 ng; |
| dNTP mixture | 0.2 nmol/µL; |
| Mg$^{2+}$ | 1.5 nmoL/µL; |
| 10 amplification buffer | 2 µL; |
| housekeeping-gene-specific primer | 10 pmol. |

The information of the selected housekeeping gene and the housekeeping-gene-specific primer were shown as following:

| Chromosome No./Housekeeping gene name | Sequence of the housekeeping-gene-specific primer (SEQ ID No:) |
|---|---|
| 1/ PRDX6 | PRDX6-S: 5'-CTTGCTTCACTCCATCAGA-3' (1)<br>PRDX6-A: 5'-CATCATCGGAAAACAGAC-3' (2) |
| 2/ RPL37a | RPL37a-S: 5'-AGTTTAGGTCAGCCTCTTAG-3' (3)<br>RPL37a-A: 5'-GGACTTTACCGTGACAGC-3' (4) |
| 4/ ADD1 | ADD1-S: 5'-TACCAGCCTGACTAGGTACAG-3' (5)<br>ADD1-A: 5'-GTCCTCCCAAGTCGGTGT-3' (6) |
| 6/ HLA-A | HLA-A-S1: 5'-GGATTACATCGCCCTGAAC-3' (7)<br>HLA-A-A1: 5'-CGTCTCCTTCCCGTTCTC-3' (8) |

-continued

| Chromosome No./Housekeeping gene name | Sequence of the housekeeping-gene-specific primer (SEQ ID No:) |
|---|---|
| 11/ RAD9A | RAD9A-S1: 5'-GGTGAAGGCTGAACCAAG-3' (9)<br>RAD9A-A1: 5'-CTGAGGCTCAATGAGAAAT-3' (10) |
| 13/ ARHGEF7 | ARHGEF7-S: 5'-AGTAGCCTTTCTCGTTTG-3' (11)<br>ARHGEF7-A: 5'-CACCACCTCCCTCCAATAGT-3' (12) |
| 14/ EIF2B2 | EIF2B2-S: 5'-GCACCTTCCTACATCTAC-3' (13)<br>EIF2B2-A: 5'-TAAGAGGCTCCAAAATCAAC-3' (14) |
| 16/ PSMD7 | PSMD7-S: 5'-AAAGTCGCCACAGGCAAGC-3' (15)<br>PSMD7-A: 5'-CGTAGCACCACAGCAAG-3' (16) |
| 19/ BCAT2 | BCAT2-S 1: 5'-GGAATCAGAGCCCACGAGT-3' (17)<br>BCAT2-A1: 5'-TATCCTTGACCGCACGAC-3' (18) |
| 21/ ATP5O | ATP5O-S1: 5'-GCACCACCAAGCCCTAAC-3' (19)<br>ATP5O-A1: 5'-TCTCCGCGATGGACACTC-3' (20) |

Note:
S: referred to forward primer; A: referred to reverse primer; 1 in S1 or A1 was only to distinguish different batches of primers.

The specific information of the above housekeeping gene may refer to *Eli Eisenberg and Erez Y. Levanon*, (2003) *Human housekeeping genes are compact. Trends in Genetics.* 19(7):362-365, which was incorporated herein by reference. The inventor has found out that, comparing with other housekeeping genes in other chromosome, the selected housekeeping genes and primers thereof in the above table may be more conveniently used in housekeeping gene detection of human cell WGA amplification product.

The condition of the PCR reaction was:

| | | |
|---|---|---|
| 95° C. | 3 min | |
| 95° C. | 30 s | |
| 55° C. | 30-40 s | 30-35 cycles |
| 72° C. | 30-50 s | |
| 72° C. | 10 min | |
| 4° C. | ∞ | |

In accordance with the method of the above housekeeping gene detection, 50 samples of human blood single cell WGA products was subjected to housekeeping gene detection. The involved 10 pairs housekeeping-gene-specific primers was correspondence with the housekeeping gene in 1, 2, 4, 6, 11, 13, 14, 16, 19 and 21# chromosome respectively. The housekeeping gene detection results with 8 pairs primers appearing bands was regarded as qualified standard of amplification products. The detection results showed that there were 34 in 50 samples of human blood single cell WGA product being qualified. And then, by using a library-construction flow of AGILENT SURESELECT® system, 50 samples of human blood single cell WGA products were subjected to exon capture to construct library, then the 50 libraries were subjected to sequencing respectively by ILLUMINA HISEQ 2000® system.

The sequencing results showed that, in 34 samples of human blood single WGA products qualified by housekeeping gene detection, the sequencing coverage rate of target region was achieved up to 60%, the success rate was achieve to 100%; while in 16 samples of human blood single WGA products unqualified by housekeeping gene detection, the sequencing coverage rate of the target region was achieved up to 60% only in one sample, and the success rate was only 6.25%. The specific results were calculated as followings:

| Sample Name | Coverage Rate | Average Depth |
|---|---|---|
| Cell-1* | 0.64 | 12 |
| Cell-2 | 0.46 | 25 |
| Cell-3* | 0.66 | 19 |
| Cell-4* | 0.61 | 10 |
| Cell-5* | 0.79 | 18 |
| Cell-6* | 0.87 | 22 |
| Cell-7 | 0.26 | 13 |
| Cell-8* | 0.63 | 16 |
| Cell-9* | 0.73 | 12 |
| Cell-10* | 0.63 | 14 |
| Cell-11 | 0.61 | 10 |
| Cell-12* | 0.97 | 21 |
| Cell-13* | 0.66 | 20 |
| Cell-14 | 0.45 | 6.9 |
| Cell-15* | 0.71 | 11 |
| Cell-16 | 0.26 | 12 |
| Cell-17* | 0.72 | 22 |
| Cell-18* | 0.62 | 17 |
| Cell-19* | 0.80 | 18 |
| Cell-20 | 0.073 | 3.5 |
| Cell-21* | 0.68 | 12 |
| Cell-22* | 0.63 | 13 |
| Cell-23* | 0.63 | 12 |
| Cell-24 | 0.23 | 4.6 |
| Cell-25* | 0.80 | 16 |
| Cell-26* | 0.85 | 24 |
| Cell-27* | 0.79 | 18 |
| Cell-28* | 0.83 | 20 |
| Cell-29 | 0.21 | 5 |
| Cell-30* | 0.83 | 16 |
| Cell-31 | 0.12 | 7 |
| Cell-32* | 0.79 | 18 |
| Cell-33* | 0.70 | 19 |
| Cell-34* | 0.64 | 18 |
| Cell-35 | 0.06 | 2 |
| Cell-36 | 0.034 | 0.5 |
| Cell-37* | 0.65 | 12 |
| Cell-38 | 0.32 | 18 |
| Cell-39* | 0.64 | 11 |
| Cell-40 | 0.43 | 13 |
| Cell-41* | 0.77 | 14 |
| Cell-42 | 0.4 | 9 |
| Cell-43* | 0.67 | 9 |
| Cell-44 | 0.32 | 13 |
| Cell-45* | 0.80 | 16 |
| Cell-46* | 0.65 | 14 |
| Cell-47 | 0.09 | 3.3 |
| Cell-48* | 0.7 | 15 |
| Cell-49* | 0.8 | 24 |
| Cell-50* | 0.87 | 17 |

Note:
*was qualified sample by detection.

According to the embodiments of the present disclosure, except for shown in EXAMPLE 1, selection of housekeeping genes in 1, 2, 4, 6, 11, 13, 14, 16, 19 and 21# chromosome, the inventor also selected another housekeeping gene which directed to other chromosomes, and designed corresponding housekeeping-gene-specific primer, the information was shown as the following table:

|  | Chromosome No. | | | | |
| --- | --- | --- | --- | --- | --- |
|  | 3 | 5 | 7 | 8 | 9 |
| Gene Name | HYAL2 | UBE2D2 | ACTB | POLR2K | ATP6V1G1 |
|  | Chromosome No. | | | | |
|  | 10 | 12 | 15 | 17 | 18 |
| Gene Name | TUBGCP2 | TXNRD1 | SRP14 | PSMB6 | MC2R |
|  | Chromosome No. | | | | |
|  | 20 | | 22 | | X |
| Gene Name | CPNE1 | | EIF3D | | CETN2 |

The results of multiple confirmations showed that in the above table each housekeeping gene was corresponding to other chromosomes except for 1, 2, 4, 6, 11, 13, 14, 16, 19 and 21# chromosome. Then, using the housekeeping-gene-specific primers in the above table, the above same single WGA product was subjected to PCR amplification as the template, eg. housekeeping gene detection. The obtained detection results showed that comparing with the above housekeeping-gene-specific genes corresponding to 1, 2, 4, 6, 11, 13, 14, 16, 19 and 21# chromosome respectively, using the specific primers of housekeeping gene in other chromosomes to perform housekeeping gene detection has poor effect, and it could not truly reflect the accuracy of the actual sequencing. This could be related to complexity of the single cell WGA amplification.

Because the chromosome DNA released from the single cell was extremely small, when performing the whole-genome amplification of the single cell, subtle environmental pollution was likely to make the amplified product being not the target product. The above results showed that using the housekeeping gene detection of the present disclosure, especially the housekeeping gene directing to human and the specific primer thereof selected by the present disclosure, the WGA product may be subjected to accurately qualified detection. After the products was qualified to meet the requirement by detection, the products was proceed to perform next steps of libray-constrution and sequencing, which may control the quality of downstream sequencing-library on machine and improve the success rate of the sequencing, thus it may avoid unnecessary waste to a great extent.

Example 3

Study on Genome of a Pollen Cell of White Flowers *Phalaenopsis* (*P. amabilis*)

The method for analyzing a genome of a single cell of the present disclosure was used to study on genome of a pollen cell of white flowers *Phalaenopsis* (*P. amabilis*), so as to make the amount of the genome amplification product meet the requirement for constructing a Solexa DNA library, thereby it may be sequenced on the sequencer.

Considering there were 3 to 5 single cells in pollen grain of the plant, so the pollen grain were separated one by one under an inverted microscope firstly, a mixture liquid of 4% cellulase and 2% pectinase having a same volume with the pollen grain was added, and placed on a vertical mixing instrument to evenly mix for 6 hours at room temperature avoiding light, so as to lyse the cell wall. Then the lysing system of the same pollen grain was added to PBS droplets on a plate, the single cell was separated under the microscope, the obtained single cell was put in a PCR tube containing 1.5 μL ALB (alkaline lysis buffer).

After that, a MDA (multiple displacement amplification) reaction was performed in accordance with the following steps: firstly, the obtained pollen grain cell was lysed at 65° C. for 10 minutes. Then, after adding 2.54 buffer D1 (prepared in EXAMPLE 1), it was incubated at room temperature for 3 minutes to denature DNA. Then adding 5 μL buffer N1 (prepared in EXAMPLE 1) to stop denaturation. The MDA reaction system may involve QIAGEN® Mini Kit or phi29 DNA polymerase product from NEB Company. After that, the system was incubated at 30° C. for 16 hours, then the system was place at 65° C. to inactivate the enzyme, so as to obtain a MDA product.

The MDA product was subjected to detection by using Quant-iT™ technique, the results showed that the MDA product with the concentration being more than 35 ng/4 was able to proceed to next-step housekeeping gene detection.

After that, the MDA product was subjected to PCR amplification by using the following housekeeping genes of orchid and specific primers thereof, so as to subject the MDA product to housekeeping gene detection

| Housekeeping genes of orchid | Length of target band | Sequence of housekeeping-gene-specific primers (SEQ ID No: ) (5'-3') |
| --- | --- | --- |
| PbGDPS-SSU | 350 bp | F: CGCACCGCCCCTCCCCTCG (21)<br>R: TTGTTAATGTAAGAAATCCTTTTTATGGGAA A(22) |
| PbGDPS-LSU | 900 bp | F: CACCATGCCCTCTGTTGCCACAACCGAGT (23)<br>R: ATTCTGCCTGTAAGCGATGTAATTCGCA (24) |
| PeActin 9 | 900 bp | F: GGCTAACAGAGAGAAGATGACC (25)<br>R: AATAGACCCTCCAATCCAGAC (26) |
| PbGDPSp 1 | 300 bp | F: GCCCATGCATCCTTAGGTCTGTTAA (27)<br>R: CGAGACAACTATGATGTGTTACGGGC (28) |
| Pe4 Cme Probe | 250 bp | F: CTATCGCTTTTGCGTTTCCAGTTC (29)<br>R: TCCCTCGCCTTCTTCATAATCCC (30) |
| Pe4-1ex-5ex | 1.2 kb | F: AAGATGGGGAGGGGAAGATAGAGATT (31)<br>R: CTTCTTCTTGTAGGTGTCCGTTTGAGT (32) |

-continued

| Housekeeping genes of orchid | Length of target band | Sequence of housekeeping-gene-specific primers (SEQ ID No: )(5'-3') |
|---|---|---|
| PbfMuta 1 | 1.7 kb | F: GCAGGACCATTCTCTTGCTGTTGGG(33)<br>R: GAGAATGACCAAGAAGATGGCAGCGG(34) |
| Pe6p | 600 bp | F: ACTGAGGGGCTGAGTGAAAAA(35)<br>R: CCTCTAGACATCTCCACCCAAAAACCGG(36) |

Note:
F: referred to forward primer; R: referred to reverse primer.

Housekeeping gene PbGDPS was related to fragrance ingredients and dissemination taste of orchid, housekeeping gene PeActin was related to drought resistance of plant to high salt environment.

The reaction system of PCR amplification were as followings:

| | |
|---|---|
| Template(10~20 μg/mL) | 1.5 μL |
| EX-Taq | 0.3 μL |
| 10X EX-taq buffer | 2 μL |
| 10 mM dNTP | 0.5 μL |
| 5 μM forward primer | 1 μL |
| 5 μM reverse primer | 1 μL |
| ddH$_2$O | 13.1 μL |
| Total Volume | 20 μL |

The PCR reaction condition was:

| | |
|---|---|
| 94° C. | 5 min |
| 30↑ cycles: | |
| 94° C. | 30 s |
| 55° C. | 45 s |
| 72° C. | 1 min |
| 72° C. | 7 min |
| 4° C. | ∞ |

Figure 7:
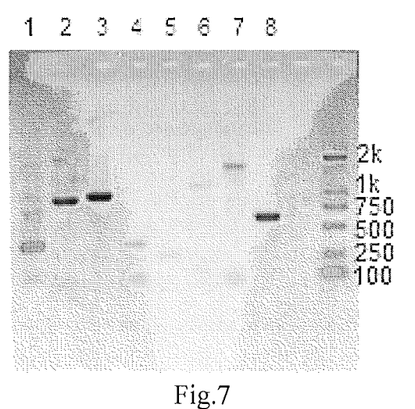
FIG. 7 is a housekeeping-gene detection result by electrophoresis according to one embodiment of the present disclosure.

After that, an agarose gel with a concentration of 1.2% was prepared, the PCR product was subjected to electrophoresis at a voltage of 100 v for 45 minutes, the result was shown in FIG. 7. When all target bands presented, it indicated that the effect of sample amplification was good. As shown in FIG. 7, each lane represented 1: PbGDPS-SSU; 2 the: PbGDPS the LSU; Each 3: PeActin the; 4: PbGDPSp 1; 5: PE4 Cme the Probe; 6: Pe4-Lex-5EX; 7: PbfMuta 1; 8: Pe6p. As can be seen from FIG. 7, the amplification effect was conform to expectations.

INDUSTRIAL APPLICABILITY

The method for analyzing the genome of the single cell and the kit of the present disclosure, may effectively used to construction of single cell DNA sequencing library and sequencing, and then may efficiently used to analysis and study of the single cell genome of higher plants and animals.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure. The whole scope of the present disclosure is given by the appended claims and any equivalents thereof.

Reference throughout this specification to "an embodiment," "some embodiments," "explanatory embodiment", "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

What is claimed is:

1. A method for analyzing a genome of a human single cell comprising the steps of:
    separating and lysing the single cell to obtain a whole-genome DNA of the cell;
    subjecting the whole-genome DNA to a whole-genome amplification to obtain a whole-genome amplification product;
    performing a PCR amplification using the whole-genome amplification product as a template and using housekeeping-gene-specific primers to detect a set of housekeeping genes of the whole-genome amplification product, wherein the set comprises PRDX6, RPL37a, ADD1, HLA-A, RAD9A, ARHGEF7, EIF2B2, PSMD7, BCAT2 and ATP5O; and
    determining whether the whole genome amplification product meets a requirement for sequencing based on the detection result,
    wherein a uniform distribution of the amplification product in each chromosome is an indication of the amplification product meeting the requirement for sequencing.

2. A method according to claim 1, wherein the whole-genome amplification comprises multi-displacement amplification (MDA) or DOP-PCR whole-genome amplification.

3. A method according to claim 1, wherein
    for PRDX6, the housekeeping-gene-specific primers have nucleotide sequences shown as SEQ ID NO:1 and SEQ ID NO:2, respectively;
    for RPL37a, the housekeeping-gene-specific primers have nucleotide sequences shown as SEQ ID NO:3 and SEQ ID NO:4, respectively;
    for ADD 1, the housekeeping-gene-specific primers have nucleotide sequences shown as SEQ ID NO:5 and SEQ ID NO:6, respectively;
    for HLA-A, the housekeeping-gene-specific primers have nucleotide sequences shown as SEQ ID NO:7 and SEQ ID NO:8, respectively;
    for RAD9A, the housekeeping-gene-specific primers have nucleotide sequences shown as SEQ ID NO:9 and SEQ ID NO:10, respectively;
    for ARHGEF7, the housekeeping-gene-specific primers have nucleotide sequences shown as SEQ ID NO:11 and SEQ ID NO:12, respectively;
    for EIF2B2, the housekeeping-gene-specific primers have nucleotide sequences shown as SEQ ID NO:13 and SEQ ID NO:14, respectively;
    for PSMD7, the housekeeping-gene-specific primers have nucleotide sequences shown as SEQ ID NO:15 and SEQ ID NO:16, respectively;
    for BCAT2, the housekeeping-gene-specific primers have nucleotide sequences shown as SEQ ID NO:17 and SEQ ID NO:18, respectively;
    for ATP5O, the housekeeping-gene-specific primers have nucleotide sequences shown as SEQ ID NO:19 and SEQ ID NO:20, respectively.

4. A method according to claim 1, wherein the whole-genome amplification product is subjected to housekeeping gene quantitative detection.

5. A method according to claim 1, further comprising constructing a DNA sequence library of the amplification product, wherein the amplification product meets the requirement for sequencing.

6. A method according to claim 5, further comprising sequencing the DNA sequence library.

* * * * *

SEQUENCE LISTING

<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer for PRDX6.

<400> SEQUENCE: 1
cttgcttcac tccatcaga

<210> SEQ ID NO 2
<211> LENGTH: 18
<212> TYPE: DNA

```
<213> ORGANISM: Artificial Sequence
<220> FEATURE:
<223> OTHER INFORMATION: Synthetic Primer for PRDX6.

<400> SEQUENCE: 2
catcatcgga aaacagac                                                      18

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer for RPL37a.

<400> SEQUENCE: 3
agtttaggtc agcctcttag                                                    20

<210> SEQ ID NO 4
<211> LENGTH: 18
<212> TYPE: DNA
<213> ORGANISM: Artificial Sequence
<220> FEATURE:
<223> OTHER INFORMATION: Synthetic Primer for RPL37a.

<400> SEQUENCE: 4
ggactttacc gtgacagc                                                      18

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer for ADD1.

<400> SEQUENCE: 5
taccagcctg actaggtaca g                                                  21

<210> SEQ ID NO 6
<211> LENGTH: 18
<212> TYPE: DNA
<213> ORGANISM: Artificial Sequence
<220> FEATURE:
<223> OTHER INFORMATION: Synthetic Primer for ADD1.

<400> SEQUENCE: 6
gtcctcccaa gtcggtgt                                                      18

<210> SEQ ID NO 7
<211> LENGTH: 19
<212> TYPE: DNA
<213> ORGANISM: Artificial Sequence
<220> FEATURE:
<223> OTHER INFORMATION: Synthetic Primer for HLA-A.

<400> SEQUENCE: 7
ggattacatc gccctgaac                                                     19

<210> SEQ ID NO 8
<211> LENGTH: 18
<212> TYPE: DNA
<213> ORGANISM: Artificial Sequence
<220> FEATURE:
<223> OTHER INFORMATION: Synthetic Primer for HLA-A.

<400> SEQUENCE: 8
cgtctccttc ccgttctc                                                      18
```

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer for RAD9A.

<400> SEQUENCE: 9
ggtgaaggct gaaccaag                                                 18

<210> SEQ ID NO 10
<211> LENGTH: 19
<212> TYPE: DNA
<213> ORGANISM: Artificial Sequence
<220> FEATURE:
<223> OTHER INFORMATION: Synthetic Primer for RAD9A.

<400> SEQUENCE: 10
ctgaggctca atgagaaat                                                19

<210> SEQ ID NO 11
<211> LENGTH: 18
<212> TYPE: DNA
<213> ORGANISM: Artificial Sequence
<220> FEATURE:
<223> OTHER INFORMATION: Synthetic Primer for ARHGEF7.

<400> SEQUENCE: 11
agtagccttt ctcgtttg                                                 18

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer for ARHGEF7.

<400> SEQUENCE: 12
caccacctcc ctccaatagt                                               20

<210> SEQ ID NO 13
<211> LENGTH: 18
<212> TYPE: DNA
<213> ORGANISM: Artificial Sequence
<220> FEATURE:
<223> OTHER INFORMATION: Synthetic Primer for EIF2B2.

<400> SEQUENCE: 13
gcaccttcct acatctac                                                 18

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer for EIF2B2.

<400> SEQUENCE: 14
taagaggctc caaaatcaac                                               20

<210> SEQ ID NO 15
<211> LENGTH: 19
<212> TYPE: DNA
<213> ORGANISM: Artificial Sequence
<220> FEATURE:

<223> OTHER INFORMATION: Synthetic Primer for PSMD7.

<400> SEQUENCE: 15
aaagtcgcca caggcaagc                                           19

<210> SEQ ID NO 16
<211> LENGTH: 17
<212> TYPE: DNA
<213> ORGANISM: Artificial Sequence
<220> FEATURE:
<223> OTHER INFORMATION: Synthetic Primer for PSMD7.

<400> SEQUENCE: 16
cgtagcacca cagcaag                                             17

<210> SEQ ID NO 17
<211> LENGTH: 19
<212> TYPE: DNA
<213> ORGANISM: Artificial Sequence
<220> FEATURE:
<223> OTHER INFORMATION: Synthetic Primer for BCAT2.

<400> SEQUENCE: 17
ggaatcagag cccacgagt                                           19

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer for BCAT2.

<400> SEQUENCE: 18
tatccttgac cgcacgac                                            18

<210> SEQ ID NO 19
<211> LENGTH: 18
<212> TYPE: DNA
<213> ORGANISM: Artificial Sequence
<220> FEATURE:
<223> OTHER INFORMATION: Synthetic Primer for ATP5O.

<400> SEQUENCE: 19
gcaccaccaa gccctaac                                            18

<210> SEQ ID NO 20
<211> LENGTH: 18
<212> TYPE: DNA
<213> ORGANISM: Artificial Sequence
<220> FEATURE:
<223> OTHER INFORMATION: Synthetic Primer for ATP5O.

<400> SEQUENCE: 20
tctccgcgat ggacactc                                            18

<210> SEQ ID NO 21
<211> LENGTH: 19
<212> TYPE: DNA
<213> ORGANISM: Artificial Sequence
<220> FEATURE:
<223> OTHER INFORMATION: Synthetic Primer for PbGDPS-SSU.

<400> SEQUENCE: 21
cgcaccgccc ctcccctcg                                           19

-continued

```
<210> SEQ ID NO 22
<211> LENGTH: 32
<212> TYPE: DNA
<213> ORGANISM: Artificial Sequence
<220> FEATURE:
<223> OTHER INFORMATION: Synthetic Primer for PbGDPS-SSU.

<400> SEQUENCE: 22
ttgttaatgt aagaaatcct ttttatggga aa                                    32

<210> SEQ ID NO 23
<211> LENGTH: 28
<212> TYPE: DNA
<213> ORGANISM: Artificial Sequence
<220> FEATURE:
<223> OTHER INFORMATION: Synthetic Primer for PbGDPS-LSU.

<400> SEQUENCE: 23
accatgccct ctgttgccac aaccgagt                                         28

<210> SEQ ID NO 24
<211> LENGTH: 28
<212> TYPE: DNA
<213> ORGANISM: Artificial Sequence
<220> FEATURE:
<223> OTHER INFORMATION: Synthetic Primer for PbGDPS-LSU.

<400> SEQUENCE: 24
attctgcctg taagcgatgt aattcgca                                         28

<210> SEQ ID NO 25
<211> LENGTH: 22
<212> TYPE: DNA
<213> ORGANISM: Artificial Sequence
<220> FEATURE:
<223> OTHER INFORMATION: Synthetic Primer for PeActin 9.

<400> SEQUENCE: 25
ggctaacaga gagaagatga cc                                               22

<210> SEQ ID NO 26
<211> LENGTH: 21
<212> TYPE: DNA
<213> ORGANISM: Artificial Sequence
<220> FEATURE:
<223> OTHER INFORMATION: Synthetic Primer for PeActin 9.

<400> SEQUENCE: 26
aatagaccct ccaatccaga c                                                21

<210> SEQ ID NO 27
<211> LENGTH: 25
<212> TYPE: DNA
<213> ORGANISM: Artificial Sequence
<220> FEATURE:
<223> OTHER INFORMATION: Synthetic Primer for PbGDPSp 1.

<400> SEQUENCE: 27
gcccatgcat ccttaggtct gttaa                                            25

<210> SEQ ID NO 28
<211> LENGTH: 26
<212> TYPE: DNA
<213> ORGANISM: Artificial Sequence
<220> FEATURE:
<223> OTHER INFORMATION: Synthetic Primer for PbGDPSp 1.
```

<400> SEQUENCE: 28
cgagacaact atgatgtgtt acgggc 26

<210> SEQ ID NO 29
<211> LENGTH: 24
<212> TYPE: DNA
<213> ORGANISM: Artificial Sequence
<220> FEATURE:
<223> OTHER INFORMATION: Synthetic Primer for Pe4 Cme Probe.

<400> SEQUENCE: 29
ctatcgcttt tgcgtttcca gttc 24

<210> SEQ ID NO 30
<211> LENGTH: 23
<212> TYPE: DNA
<213> ORGANISM: Artificial Sequence
<220> FEATURE:
<223> OTHER INFORMATION: Synthetic Primer for Pe4 Cme Probe.

<400> SEQUENCE: 30
tccctcgcct tcttcataat ccc 23

<210> SEQ ID NO 31
<211> LENGTH: 27
<212> TYPE: DNA
<213> ORGANISM: Artificial Sequence
<220> FEATURE:
<223> OTHER INFORMATION: Synthetic Primer for Pe4 -1ex-5ex.

<400> SEQUENCE: 31
aagatgggga gggggaagat agagatt 27

<210> SEQ ID NO 32
<211> LENGTH: 27
<212> TYPE: DNA
<213> ORGANISM: Artificial Sequence
<220> FEATURE:
<223> OTHER INFORMATION: Synthetic Primer for Pe4 -1ex-5ex.

<400> SEQUENCE: 32
cttcttcttg taggtgtccg tttgagt 27

<210> SEQ ID NO 33
<211> LENGTH: 25
<212> TYPE: DNA
<213> ORGANISM: Artificial Sequence
<220> FEATURE:
<223> OTHER INFORMATION: Synthetic Primer for PbfMuta 1.

<400> SEQUENCE: 33
gcaggaccat tctcttgctg ttggg 25

<210> SEQ ID NO 34
<211> LENGTH: 26
<212> TYPE: DNA
<213> ORGANISM: Artificial Sequence
<220> FEATURE:
<223> OTHER INFORMATION: Synthetic Primer for PbfMuta 1.

<400> SEQUENCE: 34
gagaatgacc aagaagatgg cagcgg 26

<210> SEQ ID NO 35
<211> LENGTH: 21

```
<212> TYPE: DNA
<213> ORGANISM: Artificial Sequence
<220> FEATURE:
<223> OTHER INFORMATION: Synthetic Primer for Pe6p.

<400> SEQUENCE: 35
actgaggggc tgagtgaaaa a                                              21

<210> SEQ ID NO 36
<211> LENGTH: 28
<212> TYPE: DNA
<213> ORGANISM: Artificial Sequence
<220> FEATURE:
<223> OTHER INFORMATION: Synthetic Primer for Pe6p.

<400> SEQUENCE: 36
cctctagaca tctccaccca aaaaccgg                                       28
```